United States Patent [19]

Lee

[11] Patent Number: 4,783,213
[45] Date of Patent: Nov. 8, 1988

[54] CERTAIN 2-(2-SUBSTITUTED BENZOYL)-4-(SUBSTITUTED OXY OR SUBSTITUTED THIO)-1,3-CYCLOHEXANEDIONES

[75] Inventor: David L. Lee, Martinez, Calif.

[73] Assignee: Stauffer Chemical Company, Westport, Conn.

[21] Appl. No.: 86,268

[22] Filed: Aug. 20, 1987

Related U.S. Application Data

[63] Continuation-in-part of Ser. No. 919,280, Oct. 16, 1986, abandoned.

[51] Int. Cl.⁴ .............................................. A01N 31/00
[52] U.S. Cl. ...................................... 71/98; 71/103; 71/105; 71/107; 71/111; 71/112; 71/118; 71/121; 71/122; 71/123; 558/396; 558/397; 558/412; 558/413; 558/414; 558/415; 560/11; 560/12; 560/13; 560/18; 560/21; 560/36; 560/52; 560/53; 564/83; 564/85; 564/86; 564/87; 564/88; 564/154; 564/155; 564/158; 564/221; 564/430; 564/440; 564/441; 564/442; 564/443; 568/29; 568/30; 568/31; 568/36; 568/37; 568/40; 568/42; 568/43; 568/64; 568/306; 568/329

[58] Field of Search .................. 71/98, 103, 105, 107, 71/111, 112, 118, 121, 122, 123; 558/396, 397, 412, 413, 414, 415; 560/11, 12, 13, 18, 21, 36, 52, 53; 564/83, 85, 86, 87, 88, 154, 155, 158, 221, 430, 440, 441, 442, 443; 568/29, 30, 31, 36, 37, 40, 42, 43, 64, 306, 329

[56] References Cited

U.S. PATENT DOCUMENTS

| | | | |
|---|---|---|---|
| 4,202,840 | 5/1980 | Gray et al. | 71/122 |
| 4,560,403 | 12/1985 | Motojima et al. | 71/106 |
| 4,681,621 | 7/1987 | Lee et al. | 71/103 |

FOREIGN PATENT DOCUMENTS

| | | | |
|---|---|---|---|
| 186118 | 7/1986 | European Pat. Off. | 71/103 |

*Primary Examiner*—Paul F. Shaver
*Assistant Examiner*—Bruce D. Gray
*Attorney, Agent, or Firm*—Edwin H. Baker

[57] ABSTRACT

Compounds of the formula

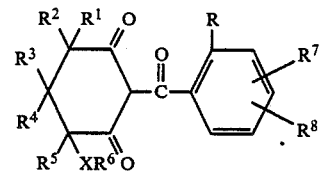

wherein
X is oxy, thio, sulfinyl or sulfonyl;
R is halogen; $C_1$–$C_2$ alkyl; $C_1$–$C_2$ alkoxy; trifluoromethoxy; difluoromethoxy; nitro; cyano; $C_1$–$C_2$ haloalkyl; $R^aSO_n$— wherein n is 0 or 2 and $R^a$ is $C_1$–$C_2$ alkyl, trifluoromethyl or difluoromethyl;
$R^1$ is hydrogen, $C_1$–$C_4$ alkyl, phenyl or substituted phenyl;
$R^2$ is hydrogen or $C_1$–$C_4$ alkyl; or
$R^1$ and $R^2$ together are $C_2$–$C_5$ alkylene;
$R^3$ is hydrogen, $C_1$–$C_4$ alkyl, phenyl or substituted phenyl with the proviso that $R^1$ and $R^3$ are not both phenyl or substituted phenyl;
$R^4$ is hydrogen or $C_1$–$C_4$ alkyl;
$R^5$ is hydrogen or $C_1$–$C_4$ alkyl;
$R^6$ is hydrogen, $C_1$–$C_4$ alkyl, $C_1$–$C_4$ haloalkyl, or phenyl;
$R^7$ and $R^8$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^bSO_n$— wherein n is the integer 0, 1 or 2; and $R^b$ is (a) $C_1$–$C_4$ alkyl; (b) $C_1$–$C_4$ alkyl substituted with halogen or cyano; (c) phenyl; or (d) benzyl; (10) —$NR^cR^d$ wherein $R^c$ and $R^d$ independently are hydrogen or $C_1$–$C_4$ alkyl; (11) $R^eC(O)$— wherein $R^e$ is $C_1$–$C_4$ alkyl or $C_1$–$C_4$ alkoxy; or (12) —$SO_2NR^cR^d$ wherein $R^c$ and $R^d$ are as defined; and (13) —$N(R^c)$-$C(O)R^d$ wherein $R^c$ and $R^d$ are as defined; and their salts.

26 Claims, No Drawings

CERTAIN 2-(2-SUBSTITUTED BENZOYL)-4-(SUBSTITUTED OXY OR SUBSTITUTED THIO)-1,3-CYCLOHEXANEDIONES

CROSS REFERENCE TO RELATED APPLICATIONS

This application is a continuation-in-part of application Ser. No. 919,280, filed Oct. 16, 1986 now abandoned.

BACKGROUND OF THE INVENTION

European patent application Nos. 135,191; 186,118; 186,119 and 186,120 relate to certain herbicidal compounds that can have the following structural formula

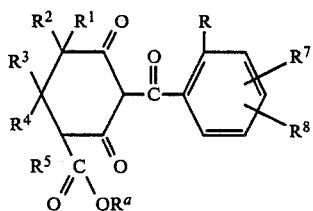

wherein R through $R^5$, $R^7$ and $R^8$ are substantially as defined below and $R^a$ is $C_1$–$C_4$ alkyl.

DESCRIPTION OF THE INVENTION

This invention relates to 2-(2-substituted benzoyl)-4-(substituted oxy or substituted thio)-1,3-cyclohexanediones and their use as herbicides.

One embodiment of this invention is an herbicidal composition comprising an herbicidally active 2-(2-substituted benzoyl)-4-(substituted oxy or substituted thio)-1,3-cyclohexanedione and an inert carrier therefor. The 5- and 6-positions of the 1,3-cyclohexanedione moiety are preferably substituted with groups hereinafter defined, most preferably with hydrogen or methyl groups. The substituted benzoyl and cyclohexanedione moieties can be further substituted, preferably with the groups hereinafter recited.

Also embodied within the scope of this invention are novel compounds having the following structural formula

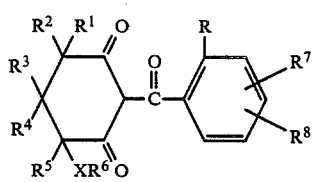

wherein

X is oxy, thio, sulfinyl or sulfonyl;

R is halogen, preferably chlorine or bromine; $C_1$–$C_2$ alkyl, preferably methyl; $C_1$–$C_2$ alkoxy, preferably methoxy; trifluoromethoxy; difluoromethoxy; nitro; cyano; $C_1$–$C_2$ haloalkyl, preferably trifluoromethyl; $R^aSO_n$— wherein n is 0 or 2, preferably 2 and $R^a$ is $C_1$–$C_2$ alkyl, preferably methyl, trifluoromethyl or difluoromethyl. Preferably, R is chlorine, bromine, $C_1$–$C_2$ alkyl, $C_1$–$C_2$ alkoxy, trifluoromethyl, cyano, nitro, $C_1$–$C_2$ alkylthio or $C_1$–$C_2$ alkylsulfonyl; more preferably chlorine, nitro, methyl, trifluoromethyl or methylsulfonyl;

$R^1$ is hydrogen; $C_1$–$C_4$ alkyl, preferably methyl; phenyl; or substituted phenyl;

$R^2$ is hydrogen or $C_1$–$C_4$ alkyl, preferably methyl; or $R^1$ and $R^2$ together are $C_2$–$C_5$ alkylene;

$R^3$ is hydrogen; $C_1$–$C_4$ alkyl, preferably methyl; phenyl; or substituted phenyl with the proviso that $R^1$ and $R^3$ are not both phenyl or substituted phenyl;

$R^4$ is hydrogen or $C_1$–$C_4$ alkyl, preferably methyl;

$R^5$ is hydrogen or $C_1$–$C_4$ alkyl, preferably methyl;

$R^6$ is hydrogen, $C_1$–$C_4$ alkyl, $C_1$–$C_4$ haloalkyl, or phenyl and $R^7$ and $R^8$ independently are (1) hydrogen; (2) halogen, preferably chlorine, fluorine or bromine; (3) $C_1$–$C_4$ alkyl, preferably methyl; (4) $C_1$–$C_4$ alkoxy, preferably methoxy; (5) trifluoromethoxy; (6) cyano; (7) nitro; (8) $C_1$–$C_4$ haloalkyl, more preferably trifluoromethyl; (9) $R^bSO_n$— wherein n is the integer 0, 1 or 2, preferably 2; and $R^b$ is (a) $C_1$–$C_4$ alkyl, preferably methyl;

(b) $C_1$–$C_4$ alkyl substituted with halogen or cyano, preferably chloromethyl, trifluoromethyl and cyanomethyl;

(c) phenyl; or (d) benzyl;

(10) —$NR^cR^d$ wherein $R^c$ and $R^d$ independently are hydrogen or $C_1$–$C_4$ alkyl;

(11) $R^eC(O)$— wherein $R^e$ is $C_1$–$C_4$ alkyl or $C_1$–$C_4$ alkoxy;

(12) —$SO_2NR^cR^d$ wherein $R^c$ and $R^d$ are as defined; or

(13) —$N(R^c)C(O)R^d$ wherein $R^c$ and $R^d$ are as defined.

Preferably $R^7$ is in the 3-position. More preferably $R^7$ is hydrogen, chlorine, fluorine, trifluoromethyl, cyano, $C_1$–$C_4$ alkoxy or $C_1$–$C_4$ thioalkyl. Most preferably, $R^7$ is hydrogen. Preferably $R^8$ is in the 4-position. Most preferably $R^8$ is halogen, cyano, trifluoromethyl, or $R^bSO_2$ wherein $R^b$ is $C_1$–$C_4$ alkyl, preferably methyl or $C_1$–$C_4$ haloalkyl, preferably chloromethyl, difluoromethyl or trifluoromethyl.

The term "$C_1$–$C_4$ alkyl" includes methyl, ethyl, n-propyl, isopropyl, n-butyl, sec-butyl, isobutyl and t-butyl. The term "halogen" includes chlorine, bromine, iodine and fluorine. The terms "$C_1$–$C_4$ alkoxy" includes methoxy, ethoxy, n-propoxy, isopropoxy, n-butoxy, sec-butoxy, isobutoxy and t-butoxy. The term "$C_1$–$C_4$ haloalkyl" includes the alkyl groups defined above under $C_1$–$C_4$ alkyl in which one or more hydrogens is replaced by chlorine, bromine, iodine or fluorine.

Salts of the above-described compounds (as defined hereinafter) are included within the scope of this invention.

The compounds of this invention can have the following four structural formulae because of tautomerism:

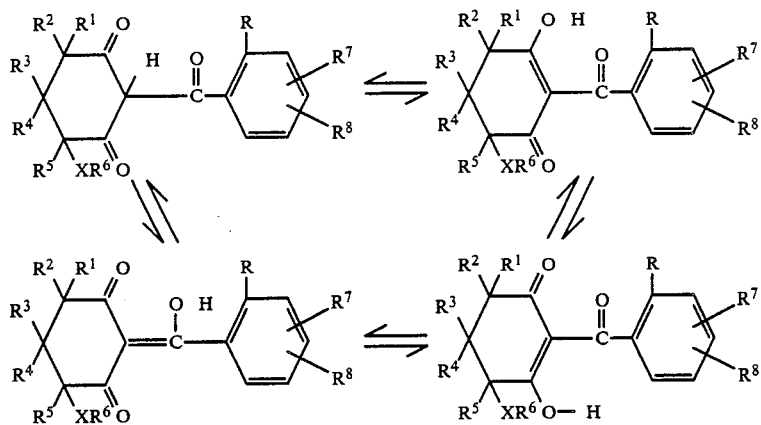

wherein R, $R^1$, $R^2$, $R^3$, $R^4$, $R^5$, $R^6$, $R^7$, $R^8$ and X are as defined above.

The circled proton on each of the four tautomers is reasonably labile. These protons are acidic and can be removed by reaction with a base to form a salt having an anion of the following four resonance forms:

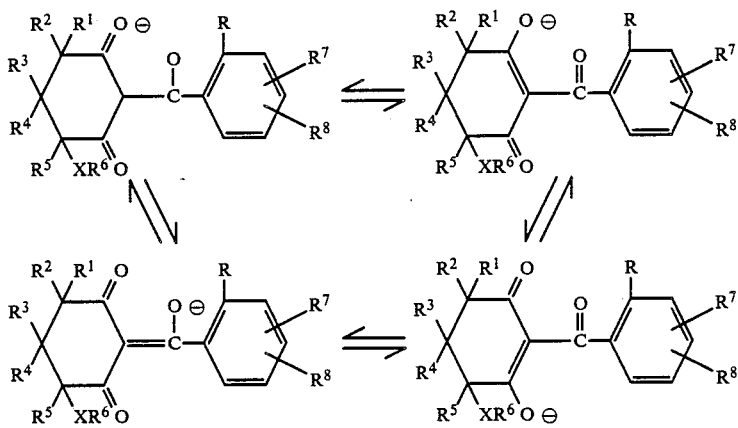

wherein R, $R^1$, $R^2$, $R^3$, $R^4$, $R^5$, $R^6$, $R^7$, $R^8$ and X are as defined above.

Examples of cations of these bases are inorganic cations such as alkali metals, e.g. lithium, sodium and potassium; the alkaline earth metals, e.g. calcium and magnesium or ammonium or organic cations such as substituted ammonium, sulfonium, sulfoxonium or phosphonium wherein the substituents are aliphatic or aromatic groups.

Those skilled in the art will recognize in considering the salts of this invention that varying degrees of association between the anion and cation will exist depending upon the nature of the cation. In some instances with a suitable cation, such as copper, the salt can exist in a chelated form.

The compounds of this invention and their salts are active herbicides of a general type. That is, they are herbicidally effective against a wide range of plant species. The method of controlling undesirable vegetation of the present invention comprises applying an herbicidally effective amount of the above-described compounds or their salts to the area where control is desired.

The compounds of the present invention can be prepared by the following two-, or, if necessary, a three-step general method.

The process proceeds via the production of an enol ester intermediate as shown in reaction (1). The final product is obtained by rearrangement of the enol ester as shown in reaction (2), or, if necessary, by subsequent oxidation of the product obtained in step (2) as shown in reaction (3).

The process is conducted in the presence of a catalytic amount of a source of cyanide anion and/or hydrogen cyanide, together with a molar excess, with respect to the enol ester, of a moderate base.

The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

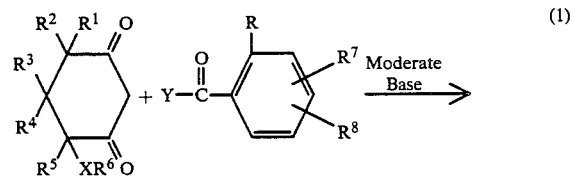

(1)

-continued

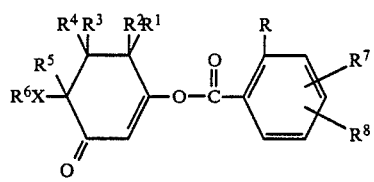

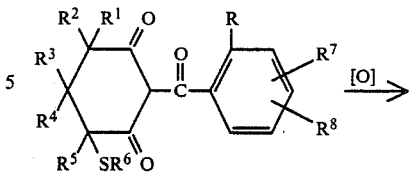  (3)

wherein R through $R^8$ and X and moderate base are as defined and Y is halogen, preferably chlorine, $C_1$-$C_4$ alkyl—C(O)—O—, $C_1$-$C_4$ alkoxy—C(O)—O— or

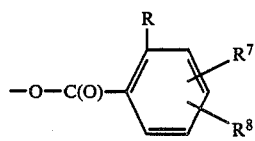

wherein R, $R^7$ and $R^8$ in this portion of the molecule are identical with those in the reactant shown above and the moderate base is as defined, preferably tri-$C_1$-$C_6$ alkylamine, alkali metal carbonate or alkali metal phosphate.

Generally, in step (1) mole amounts of the dione and substituted benzoyl reactant are used, along with a mole amount or excess of the base. The two reactants are combined in an organic solvent such as methylene chloride, toluene, ethyl acetate or dimethylformamide. The base or benzoyl reactant preferably is added to the reaction mixture with cooling. The mixture is stirred at 0° C.-50° C. until the reaction is substantially complete.

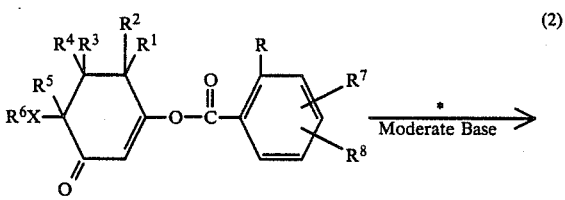 (2)

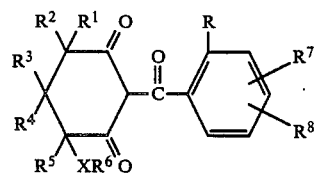

wherein the moderate base and R through $R^8$ and X are as defined above.

Generally, in step (2) a mole of the enol ester intermediate is reacted with 1 to 4 moles of the moderate base, preferably about 2 moles of moderate base and from 0.01 mole to about 0.5 mole or higher, preferably about 0.01-0.1 mole of the cyanide source. The mixture is stirred in a reaction pot until the rearrangement is substantially complete at a temperature below 50° C., preferably about 20° C. to about 40° C., and the desired product is recovered by conventional techniques.

Alternatively, certain compounds of this invention can be prepared by the following reaction:

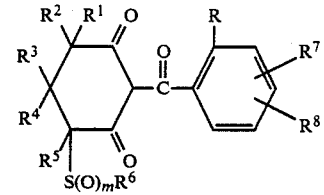

wherein R through $R^8$ are as defined, m is the integer 1 to 2 and [O] is an oxidizing agent, preferably a peroxide such as peracetic acid or m-chloroperbenzoic acid.

Generally, in reaction step (3) the substituted thio is dissolved in methylene chloride and an oxidizing agent such as m-chloroperbenzoic acid (1.1 or 2.2 equivalents) is added portionwise and the reaction mixture is stirred for 1 to 8 hours. The product may be isolated using conventional techniques.

The term "cyanide source" refers to a substance or substances which under the rearrangement conditions consists of or generates hydrogen cyanide and/or cyanide anion.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; benzaldehyde cyanohydrin; cyanohydrins of $C_2$-$C_5$ aliphatic aldehydes such as acetaldehyde cyanohydrin, propionaldehyde propionaldehyde cyanohydrin, etc.; cyclohexanone cyanohydrin; lactonitrile; zinc cyanide; di- and tri-(lower alkyl) silyl cyanides, notably dimethyl- and trimethyl-silyl cyanide; potassium ferric cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1-10 mole % of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which would cause hydrolysis of the enol ester) and that of weak bases such as N,N-dimethylaniline (which would not function effectively). Moderate bases suitable for use in this embodiment include both organic bases, e.g., trialkylamines such as triethylamine and inorganic bases such as alkali metal carbonates and phosphates. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the crown ethers.

A number of different solvents are useful in this process, depending on the nature of the acid halide or the acylated product. A preferred solvent for this reaction is 1,2-dichloroethane. Other solvents which may be employed, depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

The above described substituted benzoyl chlorides can be prepared from the corresponding substituted benzoic acids according to the teaching of *Reagents for Organic Synthesis*, Vol. I, L. F. Fieser and M. Fieser, pp. 767–769 (1967).

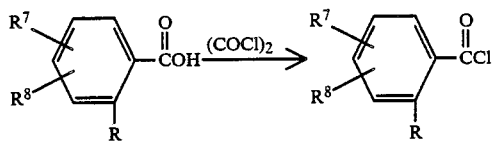

wherein R, $R^7$ and $R^8$ are as previously defined.

The substituted benzoic acids can be prepared by a wide variety of general methods according to the teaching of *The Chemistry of Carboxylic Acids and Esters*, S. Patai, editor, J. Wiley and Sons, New York, N.Y. (1969) and *Survey of Organic Synthesis*, C. A. Buehler and D. F. Pearson, J. Wiley and Sons, (1970).

The following are three representative examples of the methods described therein.

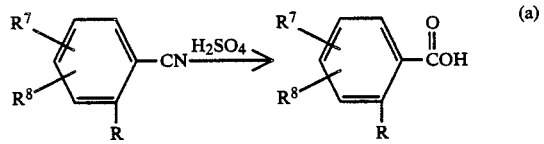

wherein R, $R^7$ and $R^8$ are as previously defined.

In reaction (a) the substituted benzonitrile is heated to reflux in aqueous sulfuric acid for several hours. The mixture is cooled and the reaction product is isolated by conventional techniques.

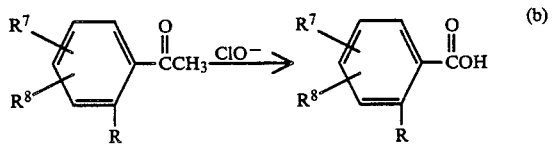

wherein R, $R^7$ and $R^8$ are as previously defined.

In reaction (b) the substituted acetophenone is heated to reflux for several hours in an aqueous hypochlorite solution. The mixture is cooled and the reaction product is isolated by conventional techniques.

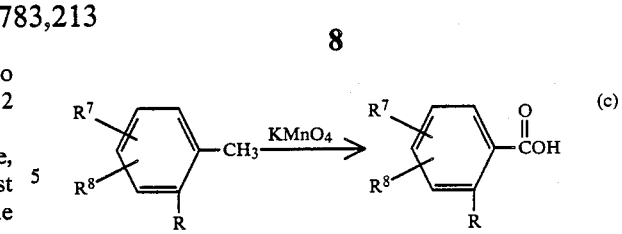

wherein R, $R^7$ and $R^8$ are as previously defined.

In reaction (c) the substituted toluene is heated to reflux in an aqueous solution of potassium permanganate for several hours. The solution is then filtered and the reaction product is isolated by conventional techniques.

The substituted 1,3-cyclohexanediones can be prepared by a wide variety of general methods according to the teachings of *Modern Synthetic Reactions*, 2nd Edition, Chapter 9, H. O. House, W. A. Benjamin, Inc., Menlo Park, CA (1972).

The following examples teach the synthesis of a representative compound of this invention.

EXAMPLE 1

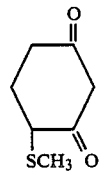

1-(Methylthio)-2-propanone [25 grams (g), 0.24 mole], ethyl acrylate (24 g, 0.24 mol), and benzyltrimethylammonium methoxide [2 milliliters (ml) of 40 wt% solution in methanol] were dissolved in toluene (100 ml). To the solution was then added a solution of sodium methoxide (77.8 g of 25 wt% in methanol, 0.36 mol) dropwise at a rate as to maintain the temperature below 35° C. After stirring an additional 2 hours at room temperature, the reaction mixture was poured into 200 ml of ice water and extracted with 100 ml of ether. The aqueous phase was acidified with 2N hydrochloric acid and extracte with ether. The ether layer was dried over magnesium sulfate, filtered, and concentrated under vacuum to afford 23.1 g of an oil. The oil was dissolved in benzene (100 ml) and the desired product slowly deposited out of the solution as waxy crystals (9.8 g).

EXAMPLE 2

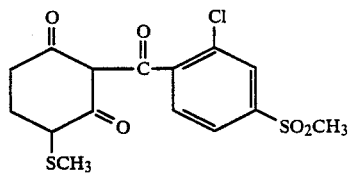

4-Methylthiocyclohexane-1,3-dione (4.4 grams, 28 ml) and 2-chloro-4-methylsulfonylbenzoyl chloride (7.1 g, 28 mmol) were dissolved in 75 (ml) of methylene chloride at room temperature. Triethylamine (5.6 g, 56 mmol) was slowly added with cooling. The reaction mixture was stirred at room temperature for 5 hours and then poured into 2N hydrochloric acid. The aqueous phase was discarded and the organic phase was dried over magnesium sulfate and then evaporated under vacuum to yield the intermediate enol ester. The enol ester was dissolved in 75 ml of acetonitrile and triethylamine (5.6 g, 56 mmol) was added all at once, followed by acetone cyanohydrin (0.8 g, 10 mmol). The reaction mixture was stirred at room temperature for 1 hour and then partitioned between 1N hydrochloric acid (100 ml) and ethyl ether (200 ml). The ether layer was washed with water and the product crystallized from the solution upon standing. Filtration of the mixture afforded 3.6 g of the desired product with a m.p. of 146°–149° C.

EXAMPLE 3

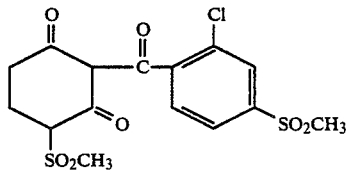

2-(2-Chloro-4-methylsulfonylbenzoyl)-4-methylthiocyclohexane-1,3-dione (1.9 g, 5 mmol) was dissolved in methylene chloride (20 ml). Meta-chloroperbenzoic acid (85%, 2.0 g, 10 mmol) was added portionwise to the stirred solution at room temperature over a period of 10 minutes. The reaction mixture was stirred at room temperature for 2 hours and then cooled to 5° C. with an ice-bath. The precipitated m-chlorobenzoic acid was removed by filtration and the product was obtained through concentration of the filtrate under vacuum. The desired product (2 g) was obtained as a tan solid with a m.p. of 175°–180° C.

The following is a table of certain selected compounds that are preparable according to the procedure described hereto. Compound numbers are assigned to each compound and are used throughout the remainder of the application.

TABLE I

| Cmpd. No. | R | $R^1$ | $R^2$ | $R^3$ | $R^4$ | $R^5$ | X | $R^6$ | $R^7$ | $R^8$ | m.p. °C. |
|---|---|---|---|---|---|---|---|---|---|---|---|
| 1 | $NO_2$ | H | H | H | H | H | O | $C_6H_5$ | H | H | oil |
| 2 | $NO_2$ | H | H | H | H | H | S | $C_6H_5$ | H | H | oil |
| 3 | $NO_2$ | H | H | H | H | H | S | $CH_3$ | H | 4-Cl | wax |
| 4 | $NO_2$ | H | H | H | H | H | S | $C_2H_5$ | H | 4-Cl | oil |
| 5a | Cl | H | H | H | H | H | S | $CH_3$ | H | 4-$SO_2CH_3$ | 146–149 |
| 6 | $NO_2$ | H | H | H | H | H | $SO_2$ | $CH_3$ | H | 4-Cl | wax |
| 7 | Cl | H | H | H | H | H | S | $C_2H_5$ | H | 4-$SO_2CH_3$ | oil |
| 8 | $NO_2$ | H | H | H | H | H | $SO_2$ | $C_2H_5$ | H | 4-Cl | wax |
| 9b | Cl | H | H | H | H | H | $SO_2$ | $CH_3$ | H | 4-$SO_2CH_3$ | 175–180 |
| 10 | $NO_2$ | H | H | H | H | H | S | $C_2H_5$ | H | 4-$CF_3$ | oil |
| 11 | Cl | H | H | H | H | H | $SO_2$ | $C_2H_5$ | H | 4-$SO_2CH_3$ | wax |
| 12 | $NO_2$ | H | H | H | H | H | $SO_2$ | $C_2H_5$ | H | 4-$CF_3$ | semi-solid |
| 13 | $NO_2$ | H | H | H | H | $CH_3$ | S | $CH_3$ | H | H | 97–101 |
| 14 | $NO_2$ | H | H | H | H | $CH_3$ | $SO_2$ | $CH_3$ | H | H | 175–179 |
| 15 | $NO_2$ | H | H | H | H | H | S | $CH_3$ | H | H | |
| 16 | $NO_2$ | H | H | H | H | H | S | $CH_3$ | H | 4-$CF_3$ | |
| 17 | $CH_3$ | H | H | H | H | H | S | $CH_3$ | H | 4-$SO_2C_2H_5$ | |
| 18 | Cl | H | H | H | H | H | S | $CH_3$ | H | 4-Cl | |
| 19 | $CF_3$ | H | H | H | H | H | S | $CH_3$ | H | H | |
| 20 | Cl | H | H | H | H | H | S | $CH_3$ | 3-$OC_2H_5$ | 4-$SO_2C_2H_5$ | |
| 21 | $CH_3$ | H | H | H | H | H | $SO_2$ | $CH_3$ | H | 4-$SO_2C_2H_5$ | |
| 22 | Cl | H | H | H | H | H | $SO_2$ | $CH_3$ | H | 4-Cl | |
| 23 | $CF_3$ | H | H | H | H | H | SO2 | $CH_3$ | H | H | |
| 24 | Cl | H | H | H | H | H | $SO_2$ | $CH_3$ | 3-$OC_2H_5$ | 4-$SO_2C_2H_5$ | |
| 25 | $NO_2$ | H | H | H | H | H | S | $CH_3$ | H | 4-$SO_2CH_3$ | oil |
| 26 | $NO_2$ | H | H | H | H | $CH_3$ | S | $CH_3$ | H | 4-$CF_3$ | 169–172 |
| 27 | Cl | H | H | H | H | $CH_3$ | S | $CH_3$ | 3-$OC_2H_5$ | 4-$SO_2C_2H_5$ | wax |
| 28 | $NO_2$ | H | H | H | H | $CH_3$ | SO | $CH_3$ | H | 4-$CF_3$ | 144–146 |
| 29 | Cl | H | H | H | H | $CH_3$ | $SO_2$ | $CH_3$ | 3-$OC_2H_5$ | 4-$SO_2C_2H_5$ | oil |
| 30 | Cl | H | H | H | H | $CH_3$ | SO | $CH_3$ | 3-$OC_2H_5$ | 4-$SO_2C_2H_5$ | wax |
| 31 | $NO_2$ | H | H | H | H | $CH_3$ | S | $CH_3$ | H | 4-$SO_2CH_3$ | 156–159 |
| 32 | $NO_2$ | H | H | H | H | $CH_3$ | $SO_2$ | $CH_3$ | H | 4-$CF_3$ | 187–190 |
| 33 | $NO_2$ | H | H | H | H | $CH_3$ | SO | $CH_3$ | H | 4-$SO_2CH_3$ | oil |
| 34 | $NO_2$ | H | H | H | H | $CH_3$ | $SO_2$ | $CH_3$ | H | 4-$SO_2CH_3$ | oil |
| 35 | $NO_2$ | H | H | H | H | H | O | $CH_3$ | H | H | oil |
| 36 | Cl | H | H | H | H | $CH_3$ | S | $CH_3$ | H | 4-$SO_2CH_3$ | 123–126 |
| 37 | Cl | H | H | H | H | $CH_3$ | $SO_2$ | $CH_3$ | H | 4-$SO_2CH_3$ | 209–213 |
| 38 | Cl | H | H | H | H | $CH_3$ | SO | $CH_3$ | H | 4-$SO_2CH_3$ | oil |
| 39 | $NO_2$ | $C_6H_5$ | H | H | H | H | S | $CH_3$ | H | H | oil |
| 40 | $NO_2$ | $C_6H_5$ | H | H | H | H | $SO_2$ | $CH_3$ | H | H | oil |
| 41 | $NO_2$ | H | H | H | H | $CH_3$ | S | $CH_3$ | H | 4-Cl | 176–179 |
| 42 | $NO_2$ | H | H | H | H | $CH_3$ | $SO_2$ | $CH_3$ | H | 4-Cl | 173–177 |
| 43 | $NO_2$ | H | H | H | H | $CH_3$ | SO | $CH_3$ | H | 4-Cl | 146–149 |
| 44 | $NO_2$ | H | H | H | H | $CH_3$ | SO | $CH_3$ | H | H | 121–124 |
| 45 | $NO_2$ | H | H | H | H | H | $SO_2$ | $CH_3$ | H | 4-$CF_3$ | oil |
| 46 | $NO_2$ | H | H | H | H | H | SO | $CH_3$ | H | 4-$CF_3$ | oil |

TABLE I-continued

| Cmpd. No. | R | $R^1$ | $R^2$ | $R^3$ | $R^4$ | $R^5$ | X | $R^6$ | $R^7$ | $R^8$ | m.p. °C. |
|---|---|---|---|---|---|---|---|---|---|---|---|
| 47 | $NO_2$ | $CH_3$ | H | H | H | $CH_3$ | S | $CH_3$ | H | H | oil |
| 48 | $NO_2$ | $CH_3$ | $CH_3$ | H | H | H | S | $CH_3$ | H | H | oil |
| 49 | $NO_2$ | $SCH_3$ | H | H | H | $CH_3$ | S | $CH_3$ | H | H | oil |
| 50 | $NO_2$ | $CH_3$ | H | H | H | $CH_3$ | SO | $CH_3$ | H | H | oil |
| 51 | $NO_2$ | $CH_3$ | H | H | H | $CH_3$ | $SO_2$ | $CH_3$ | H | H | 134–138 |
| 52 | $NO_2$ | $CH_3$ | $CH_3$ | H | H | H | SO | $CH_3$ | H | H | oil |
| 53 | $NO_2$ | $CH_3$ | H | H | H | $CH_3$ | S | $CH_3$ | H | 4-Cl | 95–98 |
| 54 | $NO_2$ | $CH_3$ | $CH_3$ | H | H | H | $SO_2$ | $CH_3$ | H | H | 198–201 |
| 55 | $NO_2$ | $SO_2CH_3$ | H | H | H | $CH_3$ | $SO_2$ | $CH_3$ | H | H | glass |
| 56 | $NO_2$ | $CH_3$ | $CH_3$ | H | H | H | S | $CH_3$ | H | 4-Cl | oil |
| 57 | $NO_2$ | $SCH_3$ | H | H | H | $CH_3$ | S | $CH_3$ | H | 4-Cl | oil |
| 58 | $NO_2$ | $CH_3$ | H | H | H | $CH_3$ | $SO_2$ | $CH_3$ | H | 4-Cl | 119–123 |
| 59 | $NO_2$ | $CH_3$ | H | H | H | $CH_3$ | SO | $CH_3$ | H | 4-Cl | oil |
| 60 | $NO_2$ | $CH_3$ | $CH_3$ | H | H | H | SO | $CH_3$ | H | 4-Cl | oil |
| 61 | $NO_2$ | $CH_3$ | $CH_3$ | H | H | H | $SO_2$ | $CH_3$ | H | 4-Cl | 134–139 |
| 62 | $NO_2$ | $CH_3$ | $SO_2CH_3$ | H | H | H | $SO_2$ | $CH_3$ | H | 4-Cl | oil |
| 63 | Cl | $CH_3$ | H | H | H | $CH_3$ | S | $CH_3$ | H | $4\text{-}SO_2CH_3$ | 140–144 |
| 64 | Cl | $CH_3$ | H | H | H | $CH_3$ | $SO_2$ | $CH_3$ | H | $4\text{-}SO_2CH_3$ | 159–164 |
| 65 | Cl | $CH_3$ | H | H | H | $CH_3$ | SO | $CH_3$ | H | $4\text{-}SO_2CH_3$ | oil |
| 66 | Cl | $CH_3$ | $CH_3$ | H | H | H | S | $CH_3$ | H | $4\text{-}SO_2CH_3$ | oil |
| 67 | Cl | $CH_3$ | $CH_3$ | H | H | H | $SO_2$ | $CH_3$ | H | $4\text{-}SO_2CH_3$ | oil |
| 68 | Cl | $CH_3$ | $CH_3$ | H | H | H | SO | $CH_3$ | H | $4\text{-}SO_2CH_3$ | oil |
| 69 | Cl | $SCH_3$ | H | H | H | $CH_3$ | S | $CH_3$ | H | $4\text{-}SO_2CH_3$ | oil |
| 70 | $NO_2$ | $CH_3$ | $CH_3$ | H | H | H | S | $CH_3$ | H | $4\text{-}CF_3$ | oil |
| 71 | Cl | H | H | H | H | $CH_3$ | S | $CH_3$ | 3-Cl | $4\text{-}SCH_3$ | 112–115 |
| 72 | Cl | H | H | H | H | $CH_3$ | $SO_2$ | $CH_3$ | 3-Cl | $4\text{-}SO_2CH_3$ | oil |
| 73 | $NO_2$ | $CH_3$ | H | H | H | $CH_3$ | S | $CH_3$ | H | $4\text{-}CF_3$ | 89–92 |
| 74 | $NO_2$ | $CH_3$ | H | H | H | $CH_3$ | $SO_2$ | $CH_3$ | H | $4\text{-}CF_3$ | oil |
| 75 | $NO_2$ | $SCH_3$ | H | H | H | $CH_3$ | S | $CH_3$ | H | $4\text{-}CF_3$ | oil |
| 76 | Cl | H | H | H | H | $CH_3$ | S | $CH_3$ | H | $4\text{-}SCH_3$ | 94–98 |
| 77 | $NO_2$ | H | H | H | H | $CH_3$ | O | H | H | H | semisolid |
| 78 | Cl | H | H | H | H | $CH_3$ | S | $CH_3$ | 3-Cl | $4\text{-}SC_2H_5$ | 96–99 |
| 79 | Cl | H | H | H | H | $CO_2CH_3$ | O | $CH_3$ | H | $4\text{-}SO_2CH_3$ | oil |
| 80 | Cl | H | H | H | H | $CH_3$ | S | $CH_3$ | 3-Cl | $4\text{-}SO_2C_2H_5$ | 139–142 |
| 81 | $NO_2$ | H | H | H | H | $CH_3$ | S | $CH_2Cl$ | H | $4\text{-}CF_3$ | 124–126 |
| 82 | Cl | H | H | H | H | $CH_3$ | S | $CH_2Cl$ | 3-Cl | $4\text{-}SO_2C_2H_5$ | 160–163 |
| 83 | $NO_2$ | H | H | H | H | $CH_3$ | S | $CH_2Cl$ | H | H | 115–117 |
| 84 | Cl | H | H | H | H | $CH_3$ | S | $CH_2Cl$ | $3\text{-}OC_2H_5$ | $4\text{-}SO_2C_2H_5$ | 107–111 |
| 85 | Cl | $CH_3$ | H | H | H | $CH_3$ | S | $CH_2Cl$ | H | $4\text{-}SO_2CH_3$ | semisolid |
| 86 | Cl | H | H | H | H | $CH_3$ | $SO_2$ | $CH_3$ | 3-Cl | $4\text{-}SO_2C_2H_5$ | 190–193 |
| 87 | Cl | $CH_3$ | $CH_3$ | H | H | H | S | $CH_3$ | $3\text{-}OC_2H_5$ | $4\text{-}SO_2C_2H_5$ | oil |
| 88 | Cl | $CH_3$ | $CH_3$ | H | H | H | $SO_2$ | $CH_3$ | $3\text{-}OC_2H_5$ | $4\text{-}SO_2C_2H_5$ | oil |
| 89c | $NO_2$ | H | H | H | H | H | S | $CH_3$ | H | $4\text{-}CF_3$ | oil |
| 90d | $NO_2$ | H | H | H | H | H | S | $CH_3$ | H | $4\text{-}CF_3$ | oil |
| 91e | $NO_2$ | H | H | H | H | H | S | $CH_3$ | H | $4\text{-}CF_3$ | 190–195 |
| 92 | Cl | $CH_3$ | H | H | H | H | S | $CH_3$ | $3\text{-}OC_2H_5$ | $4\text{-}SO_2C_2H_5$ | oil |
| 93 | Cl | $CH_3$ | H | H | H | H | $SO_2$ | $CH_3$ | $3\text{-}OC_2H_5$ | $4\text{-}SO_2C_2H_5$ | oil | a Prepared in Example 2.
b Prepared in Example 3.
c As the triethylamine salt.
d As the sodium salt.
e As the copper chelate.

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence herbicide test

On the day preceding treatment, seeds of seven different weed species are planted in loamy sand soil in individual rows using one species per row across the width of a flat. The seeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monlaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests are shown in the following Table II.

TABLE II

Post-Emergence Herbicidal Activity
Application Rate - 4.48 kg/ha

| Cmpd. No. | FT | WG | WO | AMG | VL | MD | YNG |
|---|---|---|---|---|---|---|---|
| 1 | 30 | 20 | 10 | 30 | 100 | 90 | 80 |
| 2 | 20 | 30 | 10 | 0 | 100 | 100 | 0 |
| 3 | 100 | 100 | 100 | 100 | 100 | 100 | 80 |
| 4 | 100 | 100 | 100 | 100 | 100 | 100 | 80 |
| 5 | 100 | 100 | 30 | 100 | 100 | 100 | 80 |
| 6 | 100 | 100 | 100 | 100 | 100 | 100 | 80 |
| 7 | 90 | 100 | 90 | 85 | 100 | 100 | 80 |
| 8 | 100 | 100 | 100 | 95 | 100 | 100 | 80 |
| 9 | 100 | 100 | 95 | 80 | 100 | 100 | 70 |
| 10 | 100 | 100 | 100 | 100 | 100 | 100 | 80 |
| 11 | 100 | 100 | 20 | 50 | 100 | 100 | 40 |
| 12 | 100 | 100 | 100 | 100 | 100 | 100 | 0 |
| 13 | 100 | 100 | 100 | 60 | 100 | 100 | 30 |
| 14 | 100 | 100 | 100 | 90 | 100 | 100 | 80 |
| 15 | 100 | 100 | 100 | 100 | 100 | 100 | 80 |
| 16 | 100 | 100 | 100 | 100 | 100 | 100 | 80 |
| 17 | 100 | 100 | 90 | 80 | 100 | 100 | 30 |
| 18 | 100 | 100 | 100 | 100 | 100 | 100 | 80 |
| 19 | 100 | 100 | 100 | 80 | 100 | 100 | 30 |
| 20 | 100 | 100 | 100 | 100 | 100 | 100 | 80 |
| 21 | 100 | 100 | 10 | 70 | 100 | 85 | 40 |
| 22 | 100 | 100 | 100 | 100 | 100 | 100 | 80 |
| 23 | 100 | 95 | 100 | 60 | 100 | 100 | 50 |
| 24 | 100 | 100 | 100 | 100 | 100 | 100 | 80 |
| 25 | 90 | 90 | 10 | 40 | 100 | 100 | 80 |
| 26 | 100 | 100 | 100 | 100 | 100 | 100 | 80 |
| 27 | 100 | 100 | 100 | 100 | 100 | 100 | 80 |
| 28 | 100 | 100 | 100 | 85 | 100 | 100 | 80 |
| 29 | 100 | 100 | 100 | 100 | 100 | 100 | 80 |
| 30 | 100 | 100 | 100 | 100 | 100 | 100 | 90 |
| 31 | 100 | 100 | 20 | 100 | 100 | 100 | 80 |
| 32 | 100 | 100 | 100 | 90 | 100 | 100 | 90 |
| 33 | 100 | 90 | 50 | 20 | 100 | 100 | 80 |
| 34 | 50 | 50 | 0 | 40 | 100 | 100 | 30 |
| 35 | 100 | 80 | 50 | 40 | 100 | 100 | 80 |
| 36 | 100 | 100 | 40 | 100 | 100 | 100 | 80 |
| 37 | 100 | 100 | 90 | 100 | 100 | 100 | 80 |
| 38 | 100 | 100 | 50 | 100 | 100 | 100 | 80 |
| 39 | 100 | 70 | 30 | 0 | 80 | 80 | 0 |
| 40 | 0 | 0 | 10 | 0 | 80 | 100 | 0 |
| 41 | 100 | 100 | 100 | 100 | 100 | 100 | 80 |
| 42 | 100 | 100 | 100 | 10 | 100 | 100 | 80 |
| 43 | 100 | 100 | 100 | 100 | 100 | 100 | 80 |
| 44 | 100 | 100 | 100 | 60 | 100 | 100 | 40 |
| 45 | 100 | 100 | 100 | 100 | 100 | 100 | 85 |
| 46 | 100 | 100 | 100 | 100 | 100 | 100 | 85 |
| 47 | 100 | 100 | 100 | 40 | 100 | 100 | 80 |
| 48 | 100 | 100 | 100 | 20 | 100 | 100 | 30 |
| 49 | 100 | 0 | 0 | 0 | 0 | 0 | 0 |
| 50 | 100 | 100 | 100 | 80 | 100 | 100 | 80 |
| 51 | 100 | 100 | 100 | 80 | 100 | 100 | 80 |
| 52 | 100 | 85 | 90 | 10 | 100 | 95 | 10 |
| 53 | 100 | 100 | 100 | 100 | 100 | 100 | 80 |
| 54 | 100 | 100 | 100 | 80 | 100 | 100 | 80 |
| 55 | 0 | 0 | 0 | 0 | 0 | 0 | 0 |
| 56 | 100 | 100 | 100 | 80 | 100 | 100 | 80 |
| 57 | 60 | 80 | 60 | 20 | 100 | 100 | 20 |
| 58 | 100 | 100 | 100 | 90 | 100 | 100 | 80 |
| 59 | 100 | 100 | 100 | 90 | 100 | 100 | 80 |
| 60 | 100 | 100 | 100 | 95 | 100 | 100 | 80 |
| 61 | 100 | 100 | 100 | 100 | 100 | 100 | 80 |
| 62 | 100 | 30 | 100 | 30 | 100 | 100 | 75 |
| 63 | 100 | 100 | 100 | 100 | 100 | 100 | 80 |
| 64 | 100 | 100 | 100 | 100 | 100 | 100 | 80 |
| 65 | 100 | 100 | 100 | 100 | 100 | 100 | 80 |
| 66 | 100 | 100 | 95 | 100 | 100 | 100 | 80 |
| 67 | 100 | 100 | 100 | 100 | 100 | 100 | 70 |
| 68 | 100 | 100 | 10 | 70 | 100 | 100 | 30 |
| 69 | 100 | 0 | 0 | 0 | 100 | 80 | 0 |
| 70 | 100 | 100 | 100 | 100 | 100 | 100 | 80 |
| 71 | 100 | 100 | 100 | 100 | 100 | 100 | 80 |
| 72 | 100 | 100 | 100 | 100 | 100 | 100 | 80 |
| 73 | 100 | 100 | 100 | 100 | 100 | 100 | 80 |
| 74 | 100 | 100 | 100 | 100 | 100 | 100 | 80 |
| 75 | 0 | 0 | 0 | 0 | 80 | 90 | 0 |
| 76 | 100 | 100 | 95 | 100 | 100 | 100 | 80 |
| 77 | 100 | 100 | 100 | 100 | 100 | 100 | 80 |
| 78 | 100 | 100 | 100 | 100 | 100 | 100 | 80 |
| 79 | 100 | 100 | 50 | 100 | 100 | 100 | 80 |
| 80 | 100 | 100 | 100 | 100 | 100 | 100 | 80 |
| 81 | 100 | 100 | 100 | 100 | 100 | 100 | 80 |
| 82 | 100 | 100 | 70 | 80 | 100 | 100 | 70 |
| 83 | 100 | 90 | 90 | 20 | 100 | 100 | 30 |
| 84 | 100 | 100 | 100 | 100 | 100 | 100 | 80 |
| 85 | 100 | 100 | 85 | 100 | 100 | 100 | 80 |
| 86 | 100 | 100 | 100 | 100 | 100 | 100 | 80 |
| 87 | 100 | 100 | 95 | 90 | 100 | 100 | 0 |
| 88 | 100 | 100 | 100 | 100 | 100 | 100 | 50 |
| 89 | 100 | 100 | 100 | 90 | 100 | 100 | 80 |
| 90 | 100 | 100 | 100 | 100 | 100 | 100 | 80 |
| 91 | 100 | 100 | 80 | 40 | 100 | 100 | 10 |
| 92 | 100 | 100 | 100 | 100 | 100 | 100 | 80 |
| 93 | 100 | 100 | 100 | 100 | 100 | 100 | 80 |

Post-Emergence Herbicide Test

This test is conducted in an identical manner to the testing procedure for the pre-emergence herbicide test, except the seeds of the seven different weed species are planted 10–12 days before treatment. Also, watering of the treated flats is confined to the soil surface and not to the foliage of the sprouted plants.

The results of the post-emergence herbicide test are reported in Table III.

TABLE III

Post-Emergence Herbicidal Activity
Application Rate - 4.48 kg/ha

| Cmpd. No. | FT | WG | WO | AMG | VL | MD | YNG |
|---|---|---|---|---|---|---|---|
| 1 | 10 | 20 | 0 | 20 | 60 | 30 | 30 |
| 2 | 100 | 50 | 20 | 75 | 100 | 100 | 10 |
| 3 | 100 | 100 | 80 | 80 | 90 | 100 | 60 |
| 4 | 100 | 85 | 90 | 90 | 90 | 100 | 70 |
| 5 | 80 | 85 | 80 | 90 | 100 | 100 | 70 |
| 6 | 100 | 80 | 80 | 90 | 95 | 100 | 70 |
| 7 | 80 | 80 | 80 | 80 | 80 | 100 | 30 |
| 8 | 100 | 85 | 80 | 80 | 100 | 100 | 30 |
| 9 | 100 | 90 | 100 | 80 | 100 | 100 | 40 |
| 10 | 100 | 100 | 85 | 85 | 90 | 100 | 30 |
| 11 | 85 | 95 | 100 | 90 | 100 | 100 | 10 |
| 12 | 100 | 100 | 100 | 100 | 100 | 100 | 90 |
| 13 | 100 | 100 | 100 | 100 | 100 | 100 | 30 |
| 14 | 100 | 90 | 100 | 90 | 100 | 100 | 30 |
| 15 | 100 | 100 | 100 | 85 | 95 | 90 | 10 |
| 16 | 100 | 90 | 85 | 95 | 95 | 100 | 60 |
| 17 | 90 | 85 | 75 | 60 | 80 | 60 | 0 |
| 18 | 70 | 80 | 20 | 95 | 95 | 100 | 0 |
| 19 | 50 | 30 | 30 | 90 | 80 | 20 | 0 |
| 20 | 100 | 100 | 90 | 90 | 85 | 100 | 10 |
| 21 | 100 | 100 | 100 | 90 | 60 | 60 | 0 |
| 22 | 85 | 100 | 80 | 95 | 95 | 85 | 60 |
| 23 | 20 | 20 | 20 | 60 | 90 | 85 | 10 |
| 24 | 100 | 90 | 85 | 95 | 95 | 85 | 30 |

TABLE III-continued

Post-Emergence Herbicidal Activity
Application Rate - 4.48 kg/ha

| Cmpd. No. | FT | WG | WO | AMG | VL | MD | YNG |
|---|---|---|---|---|---|---|---|
| 25 | 60 | 75 | 0 | 80 | 80 | 80 | 30 |
| 26 | 60 | 80 | 80 | 80 | 80 | 95 | 30 |
| 27 | 100 | 90 | 85 | 100 | 95 | 100 | 60 |
| 28 | 95 | 80 | 80 | 80 | 80 | 100 | 60 |
| 29 | 95 | 85 | 20 | 90 | 90 | 90 | 30 |
| 30 | 100 | 85 | 80 | 80 | 85 | 100 | 30 |
| 31 | 90 | 80 | 20 | 85 | 90 | 85 | 30 |
| 32 | 95 | 85 | 90 | 90 | 90 | 85 | 30 |
| 33 | 0 | 75 | 10 | 60 | 85 | 100 | 20 |
| 34 | 0 | 60 | 0 | 40 | 80 | 80 | 0 |
| 35 | 80 | 80 | 80 | 60 | 10 | 100 | 10 |
| 36 | 100 | 100 | 100 | 100 | 100 | 100 | 80 |
| 37 | 100 | 10 | 100 | 85 | 10 | 100 | 40 |
| 38 | 100 | 100 | 100 | 100 | 100 | 100 | 50 |
| 39 | 100 | 50 | 80 | 90 | 100 | 100 | 10 |
| 40 | 10 | 10 | 10 | 0 | 0 | 85 | 0 |
| 41 | 100 | 100 | 100 | 100 | 100 | 100 | 80 |
| 42 | 100 | 100 | 100 | 100 | 100 | 100 | 90 |
| 43 | 100 | 100 | 100 | 100 | 100 | 100 | 80 |
| 44 | 100 | 100 | 100 | 100 | 100 | 100 | 30 |
| 45 | 100 | 100 | 100 | 100 | 100 | 100 | 90 |
| 46 | 100 | 100 | 100 | 100 | 100 | 100 | 85 |
| 47 | 100 | 100 | 100 | 100 | 100 | 100 | 70 |
| 48 | 100 | 100 | 100 | 100 | 100 | 100 | 30 |
| 49 | 10 | 0 | 10 | 0 | 0 | 0 | 0 |
| 50 | 100 | 100 | 100 | 100 | 100 | 100 | 80 |
| 51 | 100 | 100 | 100 | 100 | 100 | 100 | 80 |
| 52 | 100 | 90 | 100 | 80 | 100 | 100 | 10 |
| 53 | 100 | 100 | 100 | 100 | 100 | 100 | 80 |
| 54 | 100 | 100 | 100 | 100 | 100 | 100 | 80 |
| 55 | 0 | 0 | 0 | 0 | 0 | 0 | 0 |
| 56 | 100 | 100 | 100 | 100 | 100 | 100 | 70 |
| 57 | 60 | 50 | 80 | 20 | 20 | 50 | 0 |
| 58 | 100 | 100 | 100 | 100 | 100 | 100 | 90 |
| 59 | 100 | 100 | 100 | 100 | 100 | 100 | 90 |
| 60 | 100 | 100 | 90 | 100 | 100 | 100 | 30 |
| 61 | 100 | 100 | 100 | 100 | 100 | 100 | 90 |
| 62 | 100 | 10 | 80 | 30 | 80 | 50 | 0 |
| 63 | 100 | 100 | 95 | 90 | 100 | 100 | 70 |
| 64 | 100 | 100 | 100 | 100 | 100 | 100 | 30 |
| 65 | 100 | 100 | 100 | 100 | 100 | 100 | 60 |
| 66 | 100 | 100 | 100 | 100 | 100 | 100 | 30 |
| 67 | 100 | 100 | 100 | 100 | 100 | 100 | 0 |
| 68 | 70 | 100 | 80 | 100 | 100 | 100 | 20 |
| 69 | 0 | 20 | 0 | 20 | 80 | 80 | 0 |
| 70 | 80 | 100 | 90 | 100 | 100 | 100 | 30 |
| 71 | 95 | 100 | 95 | 100 | 100 | 100 | 30 |
| 72 | 100 | 100 | 95 | 80 | 100 | 100 | 0 |
| 73 | 100 | 100 | 100 | 100 | 100 | 100 | 100 |
| 74 | 100 | 100 | 100 | 100 | 100 | 100 | 100 |
| 75 | 0 | 0 | 0 | 0 | 100 | 100 | 0 |
| 76 | 100 | 100 | 100 | 100 | 100 | 100 | 90 |
| 77 | 100 | 100 | 100 | 100 | 100 | 100 | 70 |
| 78 | 100 | 100 | 100 | 100 | 100 | 100 | 20 |
| 79 | 100 | 100 | 90 | 100 | 100 | 100 | 30 |
| 80 | 95 | 90 | 90 | 100 | 90 | 100 | 20 |
| 81 | 100 | 100 | 100 | 100 | 100 | 100 | 100 |
| 82 | 100 | 100 | 90 | 100 | 100 | 100 | 70 |
| 83 | 100 | 100 | 100 | 40 | 100 | 100 | 30 |
| 84 | 100 | 100 | 100 | 100 | 100 | 100 | 80 |
| 85 | 100 | 100 | 100 | 100 | 100 | 100 | 80 |
| 86 | 100 | 100 | 100 | 100 | 100 | 100 | 80 |
| 87 | 50 | 100 | 50 | 90 | 90 | 100 | 0 |
| 88 | 100 | 90 | 95 | 100 | 100 | 100 | 30 |
| 89 | 20 | 80 | 80 | 80 | 100 | 100 | 30 |
| 90 | 100 | 100 | 80 | 100 | 100 | 100 | 70 |
| 91 | 0 | 50 | 10 | 40 | 60 | 80 | 0 |
| 92 | 100 | 100 | 100 | 100 | 100 | 100 | 70 |
| 93 | 85 | 90 | 85 | 80 | 80 | 100 | 10 |

The compounds of the present invention and their salts are useful as herbicides and can be applied in a variety of ways at various concentrations. In practice, the compounds or salts are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds or salts can be formulated as granules of relatively large particle size, as wettable powders, as emulsifiable concentrates, as powdery dusts, as flowables, as solutions or as any of several other known types of formulations, depending upon the desired mode of application. These formulations may contain as little as about 0.5% to as much as about 95% or more by weight of active ingredient. A herbicidally effective amount depends upon the nature of the seeds or plants to be controlled and the rate of application varies from about 0.01 to approximately 10 pounds per acre, preferably from about 0.02 to about 4 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound or salt with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which may be coated with the toxicant. Granular formulations normally are prepared to contain from about to about 25% of active ingredients which may include surface-active agents such heavy aromatic naphthas, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their salts; polyhydric alcohols; polyethoxylated alcohols; esters and fatty amines; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention can be applied to the plants in the conventional manner. Thus, the dust and liquid compositions can be applied to the plant by the use of power-dusters, boom and hand sprayers and spray dusters. The compositions can also be applied from airplanes as a dust or a spray or by rope wick applications because they are effective in very low dosages. In order to modify or control growth of germinating seeds or emerging seedlings, as a typical example, the dust and liquid compositions can be applied to the soil according to conventional methods and can be distributed in the soil to a depth of at least ½ inch below the soil surface. It is not necessary that the phytotoxic compositions be mechanically admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations. In the following examples the herbicidal compound can be substituted with the herbicidal salt of the compound.

| General Formula with Ranges | | Specific Formula | |
|---|---|---|---|
| EMULSIFIABLE CONCENTRATE FORMULATIONS | | | |
| Herbicidal compound | 5–55 | herbicidal compound | 24 |
| surfactant(s) | 5–25 | proprietary blend of oil-soluble sulfonates and polyoxyethylene ethers | 10 |
| solvent(s) | 20–90 | | |
| | 100% | polar solvent | 27 |
| | | petroleum hydrocarbon | 39 |
| | | | 100% |
| WETTABLE POWDER FORMULATIONS | | | |
| herbicidal compound | 3–90 | herbicidal compound | 80 |
| wetting agent | 0.5–2 | sodium dialkyl naphthalene sulfonate | 0.5 |
| dispersing agent | 1–8 | sodium lignosulfonate | 7 |
| diluent(s) | 8.5–87 | attapulgite clay | 12.5 |
| | 100% | | 100% |
| EXTRUDED GRANULAR FORMULATIONS | | | |
| herbicidal | 1–20 | herbicidal compound | 10 |
| compound | | lignin sulfonate | 5 |
| binding agent | 0–10 | calcium carbonate | 85 |
| diluent(s) | 70–99 | | 100% |
| | 100% | | |
| FLOWABLE FORMULATIONS | | | |
| herbicidal compound | 20–70 | herbicidal compound | 45 |
| surfactant(s) | 1–10 | polyoxyethylene ether | 5 |
| suspending agent(s) | 0.05–1 | attagel | 0.05 |
| | | propylene glycol | 10 |
| | | 1,2-benzisothiazoline-3-one | 0.03 |
| antifreeze agent | 1–10 | silicone defoamer | 0.02 |
| antimicrobial agent | 1–10 | water | 39.9 |
| | | | 100% |
| antifoam agent | 0.1–1 | | |
| solvent | 7.95–77.85 | | |
| | 100% | | |

When salts are used as the active ingredient in the herbicidal compositions of this invention it is recommended to use salts that are agriculturally acceptable.

The phytotoxic compositions of this invention can also contain other additives, for example, fertilizers, other herbicides and other pesticides, used as adjuvant or in combination with any of the above-described adjuvants. Fertilizers useful in combination with the active ingredients include, for example, ammonium nitrate, urea and superphosphate.

I claim:

1. Compounds of the formula

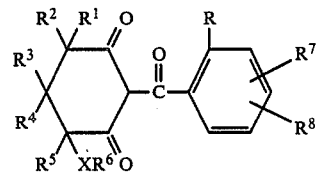

wherein
X is oxy, thio, sulfinyl or sulfonyl;
R is halogen; $C_1$–$C_2$ alkyl; $C_1$–$C_2$ alkoxy; trifluoromethoxy; difluoromethoxy; nitro; cyano; $C_1$–$C_2$ haloalkyl; $R^aSO_n$— wherein n is 0 or 2 and $R^a$ is $C_1$–$C_2$ alkyl, trifluoromethyl or difluoromethyl;
$R^1$ is hydrogen, $C_1$–$C_4$ alkyl, or phenyl;
$R^2$ is hydrogen or $C_1$–$C_4$ alkyl; or
$R^1$ and $R^2$ together are $C_2$–$C_5$ alkylene;
$R^3$ is hydrogen, $C_1$–$C_4$ alkyl, or phenyl with the proviso that $R^1$ and $R^3$ are not both phenyl;
$R^4$ is hydrogen or $C_1$–$C_4$ alkyl;
$R^5$ is hydrogen or $C_1$–$C_4$ alkyl;
$R^6$ is hydrogen, $C_1$–$C_4$ alkyl, $C_1$–$C_4$ haloalkyl, or phenyl;
$R^7$ and $R^8$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^bSO_n$— wherein n is the integer 0, 1 or 2; and $R^b$ is (a) $C_1$–$C_4$ alkyl; (b) $C_1$–$C_4$ alkyl substituted with halogen or cyano; (c) phenyl; or (d) benzyl; (10) —$NR^cR^d$ wherein $R^c$ and $R^d$ independently are hydrogen or $C_1$–$C_4$ alkyl; (11) $R^eC(O)$— wherein $R^e$ is $C_1$–$C_4$ alkyl or $C_1$–$C_4$ alkoxy; or (12) —$SO_2NR^cR^d$ wherein $R^c$ and $R^d$ are as defined; and (13) —$N(R^c)C(O)R^d$ wherein $R^c$ and $R^d$ are as defined; and their salts.

2. The compounds of claim 1 wherein R is chlorine, bromine, methyl, methoxy, nitro, trifluoromethyl or methylsulfonyl; $R^1$, $R^2$, $R^3$, $R^4$ and $R^5$ are hydrogen or methyl; $R^6$ is hydrogen, $C_1$-$C_2$ alkyl or phenyl; $R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; or (12) $SO_2NR^cR^d$ wherein $R^c$ and $R^d$ are as defined; or (13) —N—$(R^c)C(O)R^d$ wherein $R^c$ and $R^d$ are as defined.

3. The compounds of claim 2 wherein $R^7$ and $R^8$ are independently are hydrogen; chlorine; fluorine; bromine; methyl; $C_1$-$C_4$ alkoxy; trifluoromethoxy; cyano; nitro; trifluoromethyl; $R^bSO_n$— wherein n is the integer 0 or 2 and $R^b$ is methyl, chloromethyl, trifluoromethyl; ethyl or n-propyl, $R^eC(O)$— where $R^e$ is $C_1$-$C_4$ alkyl; or $SO_2NR^cR^d$ wherein $R^c$ and $R^d$ are as defined, and $R^7$ is in the 3-position and $R^8$ is in the 4-position.

4. The compounds of claim 2 wherein $R^7$ is hydrogen and $R^8$ are hydrogen, chlorine, bromine, fluorine, cyano, trifluoromethyl or $R^bSO_2$ wherein $R^b$ is $C_1$-$C_4$ alkyl or $C_1$-$C_4$ haloalkyl.

5. The compound of claim 2 wherein R is nitro; $R^1$ is hydrogen; $R^2$ is hydrogen; $R^3$ is hydrogen; $R^4$ is hydrogen; $R^5$ is hydrogen; $R^6$ is methyl; $R^7$ is hydrogen; $R^8$ is 4-chlorine; and X is thio.

6. The compound of claim 2 wherein R is nitro; $R^1$ is hydrogen; $R^2$ is hydrogen; $R^3$ is hydrogen; $R^4$ is hydrogen; $R^5$ is hydrogen; $R^6$ is methyl; $R^7$ is hydrogen; $R^8$ is 4-chlorine; and X is sulfonyl.

7. The compound of claim 2 wherein R is nitro; $R^1$ is hydrogen; $R^2$ is hydrogen; $R^3$ is hydrogen; $R^4$ is hydrogen; $R^5$ is hydrogen; $R^6$ is methyl; $R^7$ is hydrogen; $R^8$ is 4-trifluoromethyl; and X is thio.

8. The compound of claim 2 wherein R is nitro; $R^1$ is hydrogen; $R^2$ is hydrogen; $R^3$ is hydrogen; $R^4$ is hydrogen; $R^5$ is hydrogen; $R^6$ is methyl; $R^7$ is hydrogen; $R^8$ is 4-trifluoromethyl; and X is sulfonyl.

9. The compound of claim 2 wherein R is nitro; $R^1$ is hydrogen; $R^2$ is hydrogen; $R^3$ is hydrogen; $R^4$ is hydrogen; $R^5$ is methyl; $R^6$ is methyl; $R^7$ is hydrogen; $R^8$ is 4-chlorine; and X is sulfonyl.

10. The compound of claim 2 wherein R is chlorine; $R^1$ is hydrogen; $R^2$ is hydrogen; $R^3$ is hydrogen; $R^4$ is hydrogen; $R^5$ is hydrogen; $R^6$ is methyl; $R^7$ is 3-ethoxy; $R^8$ is 4—$SO_2C_2H_5$; and X is thio.

11. The compound of claim 2 wherein R is nitro; $R^1$ is hydrogen; $R^2$ is hydrogen; $R^3$ is hydrogen; $R^4$ is hydrogen; $R^5$ is hydrogen; $R^6$ is ethyl; $R^7$ is hydrogen; $R^8$ is 4-trifluoromethyl; and X is thio.

12. The compound of claim 2 wherein R is nitro; $R^1$ is hydrogen; $R^2$ is hydrogen; $R^3$ is hydrogen; $R^4$ is hydrogen; $R^5$ is hydrogen; $R^6$ is ethyl; $R^7$ is hydrogen; $R^8$ is 4-chloro; and X is thio.

13. The compounds of claim 2 wherein $R^7$ is hydrogen.

14. The compounds of claim 3 wherein $R^7$ is hydrogen.

15. The herbicidal composition comprising an herbicidally effective amount of a 2-(2-substituted benzoyl)-4-(substituted oxy or substituted thio)-1,3-cyclohexanedione compound of the formula

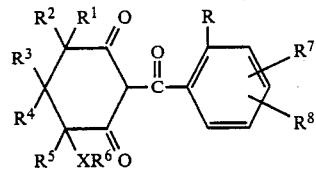

wherein
X is oxy, thio, sulfinyl or sulfonyl;
R is halogen; $C_1$-$C_2$ alkyl; $C_1$-$C_2$ alkoxy; trifluoromethoxy; difluoromethoxy; nitro; cyano; $C_1$-$C_2$ haloalkyl; $R^aSO_n$— wherein n is 0 or 2 and $R^a$ is $C_1$-$C_2$ alkyl, trifluoromethyl or difluoromethyl;
$R^1$ is hydrogen, $C_1$-$C_4$ alkyl, or phenyl;
$R^2$ is hydrogen or $C_1$-$C_4$ alkyl; or
$R^1$ and $R^2$ together are $C_2$-$C_5$ alkylene;
$R^3$ is hydrogen, $C_1$-$C_4$ alkyl, or phenyl with the proviso that $R^1$ and $R^3$ are not both phenyl;
$R^4$ is hydrogen or $C_1$-$C_4$ alkyl;
$R^5$ is hydrogen or $C_1$-$C_4$ alkyl;
$R^6$ is hydrogen, $C_1$-$C_4$ alkyl, $C_1$-$C_4$ haloalkyl, or phenyl;
$R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; or (12) —$SO_2NR^cR^d$ wherein $R^c$ and $R^d$ are as defined; and (13) —$N(R^c)C(O)R^d$ wherein $R^c$ and $R^d$ are as defined; and their salts, and an inert carrier therefore.

16. The composition of claim 15 wherein R is chlorine, bromine, methyl, methoxy, nitro, trifluoromethyl or methylsulfonyl; $R^1$, $R^2$, $R^3$, $R^4$ and $R^5$ are hydrogen or methyl; $R^6$ is hydrogen, $C_1$-$C_4$ alkyl or phenyl; $R^7$ and $R^8$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and $R^b$ is (a) $C_1$-$C_4$ alkyl; (b) $C_1$-$C_4$ alkyl substituted with halogen or cyano; (c) phenyl; or (d) benzyl; (10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; or (12) $SO_2NR^cR^d$ wherein $R^c$ and $R^d$ are as defined; or (13) —N—$(R^c)C(O)R^d$ wherein $R^c$ and $R^d$ are as defined.

17. The composition of claim 16 wherein $R^7$ and $R^8$ are independently are hydrogen; chlorine; fluorine; bromine; methyl; $C_1$-$C_4$ alkoxy; trifluoromethoxy; cyano; nitro; trifluoromethyl; $R^bSO_n$— wherein n is the integer 0 or 2 and $R^b$ is methyl, chloromethyl, trifluoromethyl, ethyl, or n-propyl; $R^eC(O)$— where $R^e$ is $C_1$-$C_4$ alkyl; or $SO_2NR^cR^d$ wherein $R^c$ and $R^d$ are as defined and $R^7$ is in the 3-position and $R^8$ is in the 4-position.

18. The composition of claim 16 wherein $R^7$ is hydrogen and $R^8$ is hydrogen, chlorine, bromine, fluorine, cyano, trifluoromethyl or $R^bSO_2$ wherein $R^b$ is $C_1$-$C_4$ alkyl or $C_1$-$C_4$ haloalkyl.

19. The composition of claim 16 wherein R is nitro; $R^1$ is hydrogen; $R^2$ is hydrogen; $R^3$ is hydrogen; $R^4$ is hydrogen; $R^5$ is hydrogen; $R^6$ is methyl; $R^7$ is hydrogen; $R^8$ is 4-chlorine; and X is thio.

20. The composition of claim 16 wherein R is nitro; $R^1$ is hydrogen; $R^2$ is hydrogen; $R^3$ is hydrogen; $R^4$ is hydrogen; $R^5$ is hydrogen; $R^6$ is methyl; $R^7$ is hydrogen; $R^8$ is 4-chlorine; and X is sulfonyl.

21. The composition of claim 16 wherein R is nitro; $R^1$ is hydrogen; $R^2$ is hydrogen; $R^3$ is hydrogen; $R^4$ is hydrogen; $R^5$ is hydrogen; $R^6$ is methyl; $R^7$ is hydrogen; $R^8$ is 4-trifluoromethyl; and X is thio.

22. The composition of claim 16 wherein R is nitro; $R^1$ is hydrogen; $R^2$ is hydrogen; $R^3$ is hydrogen; $R^4$ is hydrogen; $R^5$ is hydrogen; $R^6$ is methyl; $R^7$ is hydrogen; $R^8$ is 4-trifluoromethyl; and X is sulfonyl.

23. The composition of claim 16 wherein R is nitro; $R^1$ is hydrogen; $R^2$ is hydrogen; $R^3$ is hydrogen; $R^4$ is hydrogen; $R^5$ is hydrogen; $R^6$ is methyl; $R^7$ is hydrogen; $R^8$ is 4-chlorine; and X is sulfonyl.

24. The composition of claim 16 wherein R is chlorine; $R^1$ is hydrogen; $R^2$ is hydrogen; $R^3$ is hydrogen; $R^4$ is hydrogen; $R^5$ is hydrogen; $R^6$ is methyl; $R^7$ is 3-ethoxy; $R^8$ is 4—$SO_2C_2H_5$; and X is thio.

25. The composition of claim 16 wherein R is nitro; $R^1$ is hydrogen; $R^2$ is hydrogen; $R^3$ is hydrogen; $R^4$ is hydrogen; $R^5$ is hydrogen; $R^6$ is ethyl; $R^7$ is hydrogen; $R^8$ is 4-trifluoromethyl; and X is thio.

26. The composition of claim 16 wherein R is nitro; $R^1$ is hydrogen; $R^2$ is hydrogen; $R^3$ is hydrogen; $R^4$ is hydrogen; $R^5$ is hydrogen; $R^6$ is ethyl; $R^7$ is hydrogen; $R^8$ is 4-chloro; and X is thio.

* * * * *